US006924108B2

(12) United States Patent
Erikson et al.

(10) Patent No.: US 6,924,108 B2
(45) Date of Patent: Aug. 2, 2005

(54) NUCLEIC ACID BINDING ENHANCEMENT BY CONJUGATION WITH NUCLEOTIDES, NUCLEOSIDES, BASES AND/OR THEIR ANALOGUES

(75) Inventors: Glen H. Erikson, Providenciales (TC); Jasmine I. Daksis, Richmond Hill (CA)

(73) Assignee: Ingeneus Corporation, Bridgetown (BB)

(*) Notice: Subject to any disclaimer, the term of this patent is extended or adjusted under 35 U.S.C. 154(b) by 0 days.

(21) Appl. No.: 10/080,767

(22) Filed: Feb. 22, 2002

(65) Prior Publication Data

US 2002/0127590 A1 Sep. 12, 2002

Related U.S. Application Data

(63) Continuation-in-part of application No. 09/909,496, filed on Jul. 20, 2001, now Pat. No. 6,656,692, which is a continuation-in-part of application No. 09/664,827, filed on Sep. 19, 2000, and a continuation-in-part of application No. 09/613,263, filed on Jul. 10, 2000, now Pat. No. 6,420,115, which is a continuation-in-part of application No. 09/468,679, filed on Dec. 21, 1999, now Pat. No. 6,403,313.
(60) Provisional application No. 60/281,547, filed on Apr. 4, 2001.

(51) Int. Cl.⁷ ............................ C12Q 1/68; C07H 21/04
(52) U.S. Cl. ...................... 435/6; 536/23.1; 536/24.32; 536/24.33
(58) Field of Search ...................... 435/6, 91.1, 91.2; 436/94; 536/25.3, 23.1, 24.32

(56) References Cited

U.S. PATENT DOCUMENTS

| | | | |
|---|---|---|---|
| 4,220,450 A | 9/1980 | Maggio | |
| 4,876,187 A | 10/1989 | Duck et al. | |
| 4,963,477 A | 10/1990 | Tchen | |
| 5,011,769 A | 4/1991 | Duck et al. | |
| 5,030,557 A * | 7/1991 | Hogan et al. ............... | 435/6 |
| 5,332,659 A | 7/1994 | Kidwell | |
| 5,403,711 A | 4/1995 | Walder et al. | |
| 5,538,848 A | 7/1996 | Livak et al. | |
| 5,539,082 A | 7/1996 | Nielsen et al. | |
| 5,558,998 A | 9/1996 | Hammond et al. | |
| 5,660,988 A | 8/1997 | Duck et al. | |
| 5,705,346 A | 1/1998 | Okamoto et al. | |
| 5,707,801 A | 1/1998 | Bresser et al. | |
| 5,720,928 A | 2/1998 | Schwartz | |
| 5,731,146 A | 3/1998 | Duck et al. | |
| 5,770,365 A | 6/1998 | Lane et al. | |
| 5,800,984 A | 9/1998 | Vary | |
| 5,800,992 A | 9/1998 | Fodor et al. | |
| 5,814,447 A | 9/1998 | Ishiguro et al. | |
| 5,814,516 A | 9/1998 | Vo-Dinh | |
| 5,824,477 A | 10/1998 | Stanley | |
| 5,824,557 A | 10/1998 | Burke et al. | |
| 5,846,729 A * | 12/1998 | Wu et al. ............... | 435/6 |
| 5,861,124 A | 1/1999 | Hosoi et al. | |
| 5,874,555 A | 2/1999 | Dervan et al. | |
| 5,888,739 A | 3/1999 | Pitner et al. | |
| 5,912,332 A | 6/1999 | Agrawal et al. | |
| 5,948,897 A | 9/1999 | Sen et al. | |
| 6,013,443 A | 1/2000 | Heilig et al. | |
| 6,017,709 A | 1/2000 | Hardin et al. | |
| 6,027,880 A | 2/2000 | Cronin et al. | |
| 6,046,004 A | 4/2000 | Wu et al. | |
| 6,048,690 A * | 4/2000 | Heller et al. ............... | 435/6 |
| 6,060,242 A | 5/2000 | Nie et al. | |
| 6,107,078 A | 8/2000 | Keese et al. | |
| 6,117,657 A | 9/2000 | Usman et al. | |
| 6,130,038 A * | 10/2000 | Becker et al. ............... | 435/6 |
| 6,147,198 A | 11/2000 | Schwartz | |
| 6,251,591 B1 | 6/2001 | Wu et al. | |
| 6,255,050 B1 | 7/2001 | Nie et al. | |
| 6,255,469 B1 | 7/2001 | Seeman et al. | |
| 6,265,170 B1 | 7/2001 | Picard et al. | |
| 6,287,772 B1 | 9/2001 | Stefano et al. | |
| 6,312,925 B1 * | 11/2001 | Meyer, Jr. et al. ......... | 435/91.1 |

FOREIGN PATENT DOCUMENTS

| | | |
|---|---|---|
| GB | 2333359 A | 7/1999 |
| GB | 2338301 A | 12/1999 |
| WO | WO 97/45539 A1 | 12/1997 |
| WO | WO 00/20633 A1 | 4/2000 |

OTHER PUBLICATIONS

Astract of JP 5237000, Yoshitami (Sep. 17, 1993).
Baran et al., *Nucleic Acids Research* 25:297–303 (1997).
Bohmann et al., *Science*, 238:1386–1392 (Dec. 1987).
Carlsson et al., 380 *Nature* 207 (Mar. 21, 1996).
Chan et al., *J. Mol. Med.* 75 Issue 4:267–282 (1997).
Dalrymple et al., *Nucleic Acids Research*, vol. 13, No. 21, pp. 7865–7879 (1985).
Durland et al., *Biochemistry*, 30:9246–9255 (1991).
Egholm et al., 365 *Nature* 566 (Oct. 7, 1993).
Floris et al., 260 *Eur. J. Biochem.* 801–809 (1999).
Hill et al., *Methods in Enzymology*, 278:390–416 (1997).
Johansen and Jacobsen, *J Biomol Struct Dyn*, 16(2):205–22 (Oct 1998) (Abstract).

(Continued)

*Primary Examiner*—BJ Forman
*Assistant Examiner*—Cynthia Wilder
(74) *Attorney, Agent, or Firm*—Caesar, Rivise, Bernstein, Cohen & Pokotilow, Ltd.

(57) ABSTRACT

An improved method of forming a specific complex between a probe containing probe nucleobases and a target containing target nucleobases, includes mixing the probe and the target under hybridizing conditions, wherein the probe and/or the target is conjugated to a blocking agent, which enhances the avidity and/or specificity of hybridization, whether by Watson-Crick motif or by homologous binding motif. The blocking agent contains at least one nucleobase and can be, e.g., a free nucleobase, a nucleoside or a nucleotide.

46 Claims, 2 Drawing Sheets

OTHER PUBLICATIONS

Kadonaga et al., *Cell*, 51:1079–1090 (Dec. 24, 1987).
Kukreti et al. 25 *Nucleic Acids Research* 4264–4270 (1997).
Marsh et al., *Nucleic Acids Research*, 23:696–700 (1995).
Marsh et al., *Biochemistry* 33:10718–10724 (1994).
Mazumder et al., *Biochemistry* 35:13762–13771 (1996).
Rocher, Christophe et al., *Nucleic Acids Research*, "Initiation of DNA replication by DNA polymerases from primers forming a triple helix," 2001, vol. 29, No. 16, 3320–3326.
Sen et al., *Nature* 334:364–366 (Jul. 28, 1988).
Sen et al., *Biochemistry* 31:65–70 (1992).
Sturm et al., *Genes & Development*, 2:1582–1599 (1988).
Tomac et al., 118 *J. Am. Chem. Soc.* 5544–5552 (1996).
Watson, James, "A Personal Account of the Discovery of the Structure of DNA," (1968).
Williamson et al., *Cell* 59:871–880 (Dec. 1, 1989).
Wilson et al., *Cell*, 74:115–125 (Jul. 16, 1993).
Zhurkin et al., *J. Mol. Biol.*, vol. 239, 181–200 (1994).
Riccelli et al., "Hybridization of single–stranded DNA targets to immobilized complementary DNA probes: comparison of hairpin versus linear capture probes." Nucleic Acids Res Feb. 15, 2001;29(4):996–1004.

* cited by examiner

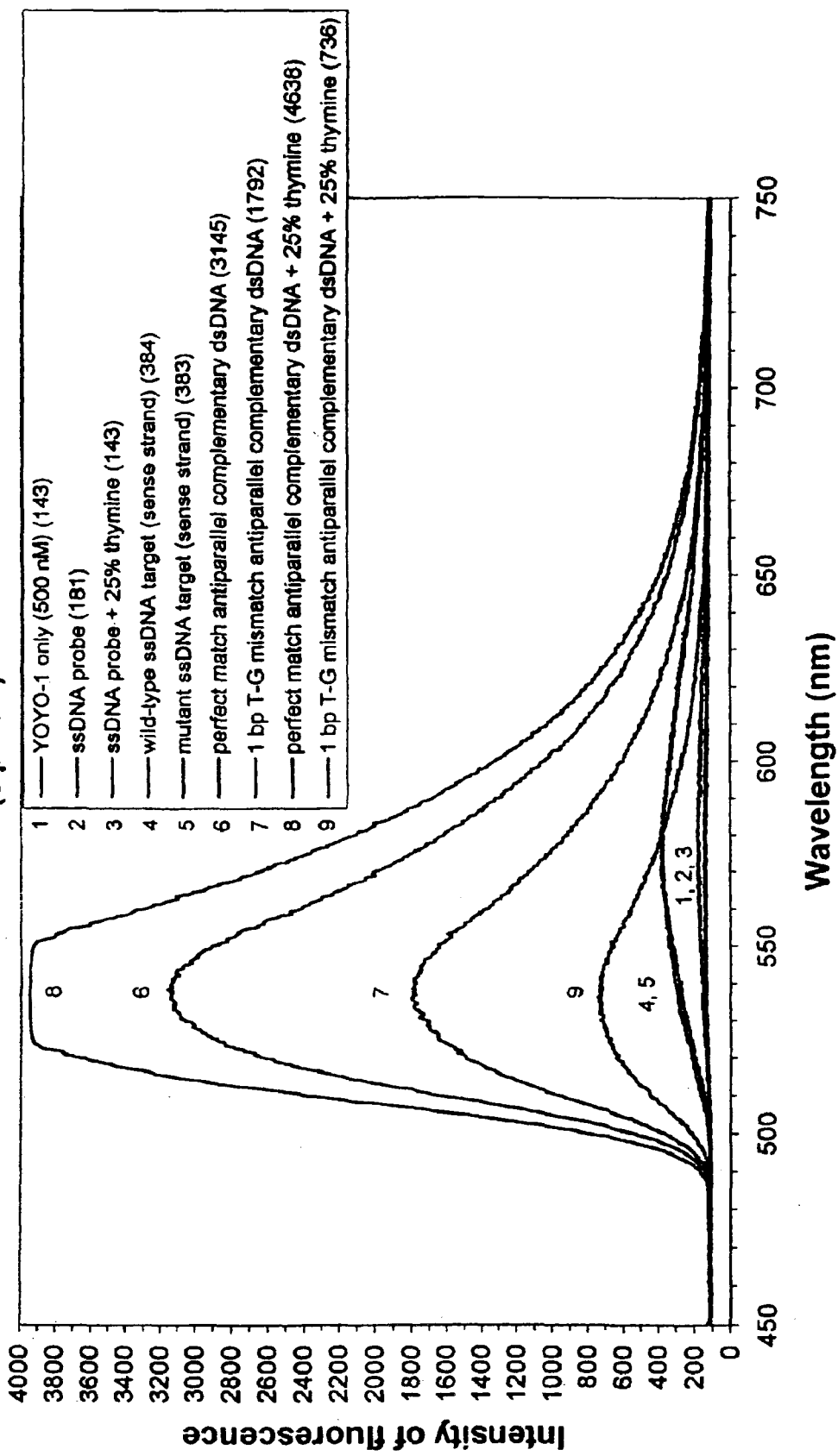

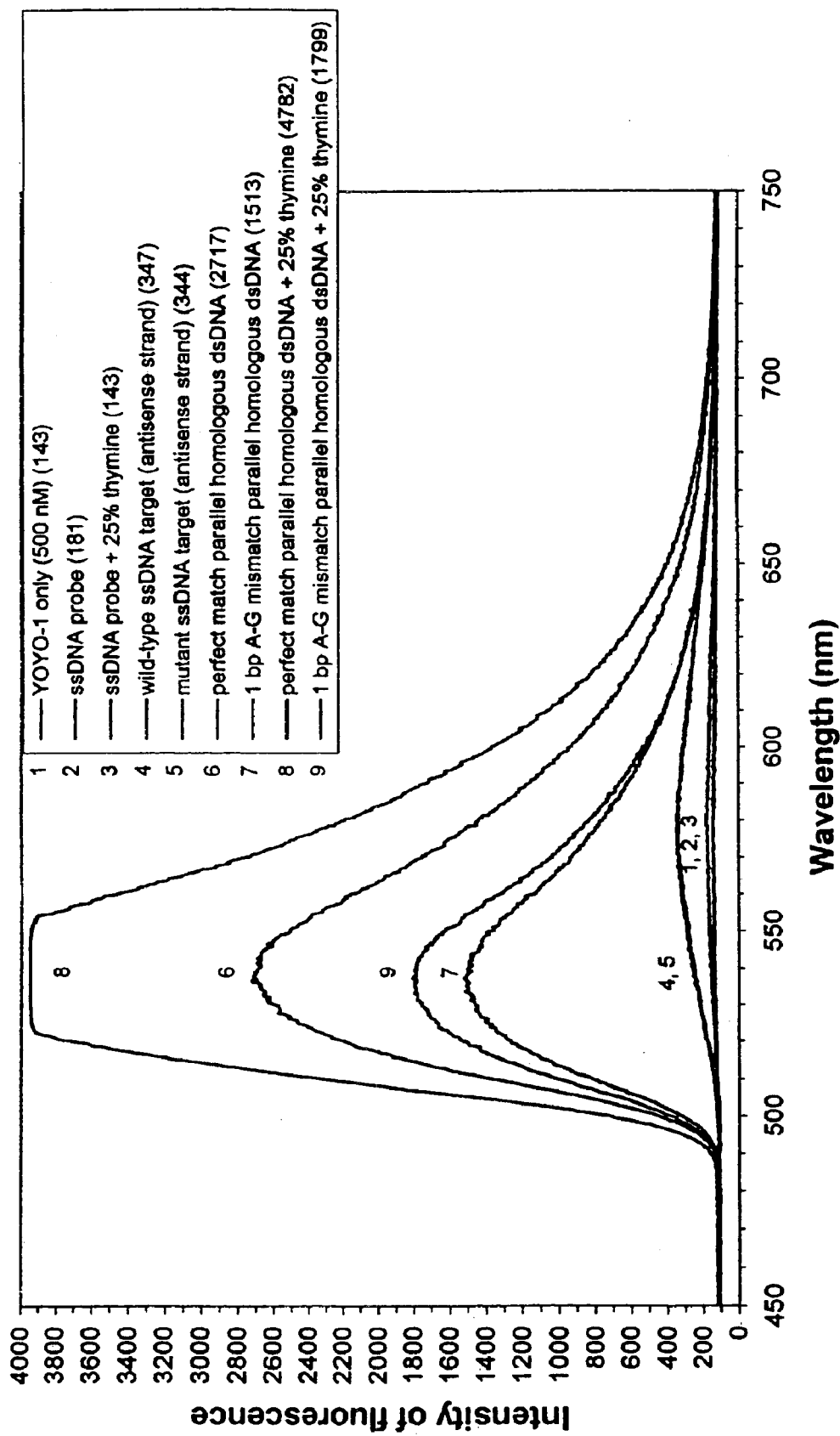

FIG. 1B. Binding of 15-mer ssDNA probe (2 pmole) and 50-mer parallel homologous ssDNA target (2 pmole) in the presence of YOYO-1 and thymine (3 pmole)

1 — YOYO-1 only (500 nM) (143)
2 — ssDNA probe (181)
3 — ssDNA probe + 25% thymine (143)
4 — wild-type ssDNA target (antisense strand) (347)
5 — mutant ssDNA target (antisense strand) (344)
6 — perfect match parallel homologous dsDNA (2717)
7 — 1 bp A-G mismatch parallel homologous dsDNA (1513)
8 — perfect match parallel homologous dsDNA + 25% thymine (4782)
9 — 1 bp A-G mismatch parallel homologous dsDNA + 25% thymine (1799)

SEQUENCE LISTING

```
<160> NUMBER OF SEQ ID NOS: 3

<210> SEQ ID NO 1
<211> LENGTH: 50
<212> TYPE: DNA
<213> ORGANISM: Artificial Sequence
<220> FEATURE:
<223> OTHER INFORMATION: Excerpt based on Exon 10 of Human Cystic
      Fibrosis Gene

<400> SEQUENCE: 1
gagcaccatg acagacactg tcatctctgg tgtgtcctac gatgactctg            50

<210> SEQ ID NO 2
<211> LENGTH: 50
<212> TYPE: DNA
<213> ORGANISM: Artificial Sequence
<220> FEATURE:
<223> OTHER INFORMATION: Excerpt based on Exon 10 of Human Cystic
      Fibrosis Gene

<400> SEQUENCE: 2
gagcaccatg acagacactg tcatctttgg tgtgtcctac gatgactctg            50

<210> SEQ ID NO 3
<211> LENGTH: 15
<212> TYPE: DNA
<213> ORGANISM: Artificial Sequence
<220> FEATURE:
<223> OTHER INFORMATION: Excerpt based on Exon 10 of Human Cystic
      Fibrosis Gene

<400> SEQUENCE: 3
caccagagat gacag                                                  15
```

NUCLEIC ACID BINDING ENHANCEMENT BY CONJUGATION WITH NUCLEOTIDES, NUCLEOSIDES, BASES AND/OR THEIR ANALOGUES

CROSS-REFERENCE TO RELATED APPLICATIONS

This application claims the benefit of U.S. Provisional Application No. 60/281,547, filed Apr. 4, 2001, and is a continuation-in-part of U.S. patent application Ser. No. 09/909,496, filed Jul. 20, 2001 now U.S. Pat. No. 6,656,692, which is a continuation-in-part of U.S. patent application Ser. No. 09/664,827, filed Sep. 19, 2000, and is also a continuation-in-part of U.S. patent application Ser. No. 09/613,263, filed Jul. 10, 2000 now U.S. Pat. No. 6,420,115, which is a continuation-in-part of U.S. patent application Ser. No. 09/468,679, filed Dec. 21, 1999 now U.S. Pat. No. 6,403,313, the disclosures of which are incorporated by reference herein in their entireties.

BACKGROUND OF THE INVENTION

1. Field of Invention

This invention relates to hybridization of nucleic acids and/or nucleic acid analogues, particularly in the context of genetic diagnostics and therapeutics.

2. Description of Related Art

Although there is a recent report that hybridization efficiency can be enhanced by probes containing hairpins proximal to the target-binding base sequence under certain conditions (Riccelli et al., "Hybridization of single-stranded DNA targets to immobilized complementary DNA probes: comparison of hairpin versus linear capture probes." Nucleic Acids Res 2001 Feb. 15;29(4):996–1004; see also U.S. Pat. No. 5,770,365 to Lane et al.) it is generally believed that hybridization efficiency is compromised by hairpin formation, wherein a first base sequence of a probe bonds with a second base sequence of the probe complementary to the first base sequence. As a result the probe is less available to complex with target base sequences in the test medium. Single stranded RNA similarly forms hairpins and can therefore be difficult to assay.

While increasing stringency tends to diminish the formation of hairpins, it also diminishes the potential of all hybridization events.

It is the constant preoccupation of researchers to discover means of enhancing binding efficiency of nucleic acids and to mitigate the consequences of unwanted hairpin secondary structure. It is therefore desired to provide such means.

It is further desired to hinder probe hairpin formation while substantially preserving, and preferably enhancing, the sensitivity of the probe for the target base sequence.

All references cited herein are incorporated herein by reference in their entireties.

BRIEF SUMMARY OF THE INVENTION

The invention provides an improved method of forming a complex between a probe containing probe nucleobases and a target containing target nucleobases, comprising mixing the probe and the target under hybridizing conditions, wherein at least one blocking agent comprising at least one nucleobase is conjugated to said probe and/or said target prior to hybridizing said probe with said target, said conjugation enhancing an avidity and/or a specificity of said hybridizing.

DETAILED DESCRIPTION OF THE INVENTION

The invention flows from the inventor's discovery that the use of hairpin blocking agents to prevent hairpin formation can have a generally positive effect on hybridization complex formation, despite the teachings of Riccelli et al., supra, to the contrary. Such agents also improve hybridization complexes comprising a plurality of nucleobase strands, which do not have secondary structure or hairpin potential. The invention herein disclosed was driven by the desire to develop means of mitigating hairpin structure in probe strands. It was unexpectedly discovered that the conjugation herein disclosed enhances nucleic acid binding generally.

The target can be single-stranded or double-stranded, such that hybridization is based on the conventional double-stranded model or the triplex model disclosed in U.S. patent application Ser. No. 09/468,679, filed Dec. 21, 1999. Suitable targets include, e.g., ssDNA, RNA, dsDNA, dsRNA, DNA:RNA, genomic nucleic acid, nucleic acid amplicons and analogues thereof. In embodiments, the target is a single molecule of genomic nucleic acid elongated and fixed to a planar surface.

The target and probe need not be homopolymeric to achieve hybridization in the case of triplex formation. Thus, in embodiments, the probe nucleobases are arranged in a probe sequence of interspersed purines and pyrimidines, and the target nucleobases are arranged in a target sequence at least partially complementary to the probe sequence.

Suitable probes for use in the inventive assay include, e.g., ssDNA, RNA, PNA, LNA and other nucleic acid analogues having uncharged, positively-charged, sugar phosphate and/or peptide backbones. Probe sequences having any length from 8 to 20 bases are preferred since this is the range within which the smallest unique RNA or DNA sequences of prokaryotes and eukaryotes may be identified. Probes of 12 to 18 bases are considered particularly preferred since this is the length of the smallest unique base sequences in the human genome. In embodiments, probes of 5 to 30 bases are most preferred. However, a plurality of shorter probes can be used to detect a nucleotide sequence having a plurality of non-unique target sequences therein, which combine to uniquely identify the nucleotide sequence. The length of the probe can be selected to match the length of the target.

The probe can comprise a heteropolymeric sequence of nucleobases. Thus, in certain embodiments, the probe nucleobases are at least two different naturally-occurring nucleobases selected from the group consisting of A, T, C, G, U and rare naturally occurring (e.g., non-canonical) bases. In other embodiments, at least some of the probe nucleobases are synthetic analogues of the naturally-occurring nucleobases. It should be apparent from the foregoing that the term "nucleobase" as used herein encompasses the bases A, T, C, G and U and natural and synthetic analogues thereof.

The probe can be chiral or achiral.

The directionality of the probe can be parallel or antiparallel to that of the target.

The invention enhances nucleic acid binding and mitigates the consequences of hairpin formation (i.e., self-hybridization and folding of the probe and/or target) through the use of at least one blocking agent comprising a base conjugated to the probe and/or to the target. The blocking agent is preferably a single naturally-occurring nucleobase selected from the group consisting of A, T, C, G and U, other naturally occurring bases or a synthetic nucleobase analogue. The blocking agent is preferably provided in the form of a free base, a nucleoside, or a nucleotide. At least one of the nucleobases on the target and/or the probe is blocked with a blocking agent.

Complexes of the invention can be provided for analytic, diagnostic, therapeutic and/or engineering purposes. The complexes can be used to analyze, diagnose and/or treat conditions associated with infection by an organism or virus. The organism or virus can be quantitated, if desired.

Complexes of the invention can be formed under conventional duplex hybridization conditions, under triplex hybridization conditions or under conditions of in situ hybridization.

The complex can be formed under non-competitive or competitive conditions. For example, the complex can be formed in a presence of a primary probe and at least one other probe containing a sequence of nucleobases complementary to a secondary target sequence different from a primary target sequence of said target. In embodiments, the other probe can differ from the primary probe by only a single nucleobase. The other probe can have a backbone composition the same as or different from that of the primary probe. In embodiments, the nucleobases of the other probe are unconjugated, partially conjugated or fully conjugated to blocking bases. The other probe can be provided in the test medium in a concentration less than, more than or equal to the concentration of the probe. The other probe can form a complex with the target alone, or with the target and primary probe. Non-specific binding of the primary probe and/or the other probe can be suppressed by practicing the method herein disclosed, if desired.

In preferred embodiments, the invention provides a rapid, sensitive, environmentally friendly, and safe method for detecting binding between a target and a probe. In embodiments, the probe or the target is bound to a substrate, surface or biochip. In other embodiments, neither the probe nor the target is bound to a support, but rather, the complex is formed in solution. In embodiments, at least one of the probe and the target is dehydrated prior to being added to a test medium.

The complex is preferably detected by a change in at least one label. The at least one label can be attached to the probe and/or the target, and/or can be free in the test medium. The at least one label can comprise at least two moieties.

The label is preferably at least one member selected from the group consisting of a spin label, a fluorophore, a chromophore, a chemiluminescent agent, an electrochemiluminescent agent, a radioisotope, an enzyme, a hapten, an antibody and a labeled antibody. Preferably, the complex is detected by at least one emission from the label or by monitoring an electronic characteristic of the complex.

The labeled antibody can be, e.g., a labeled anti-nucleic acid/nucleic acid antibody, which can be labeled with a detectable moiety selected from the group consisting of a fluorophore, a chromophore, a spin label, a radioisotope, an enzyme, a hapten, a chemiluminescent agent and an electrochemiluminescent agent.

The complex can be detected under at least one varied condition, such as disclosed in U.S. Pat. No. 6,265,170 to Picard et al. Suitable varied conditions include, e.g., (a) a change in nonaqueous components of the test medium, (b) a change in a pH of the test medium, (c) a change in a salt concentration of the test medium, (d) a change of an organic solvent content of the test medium, (e) a change in a formamide content of the test medium, (f) a change in a temperature of the test medium, and (g) a change in chaotropic salt concentration in the test medium. In addition, the varied condition can be the application of a stimulus, such as, e.g., electric current (DC and/or AC), photon radiation (e.g., laser light), or electromagnetic force. The stimulus can be applied constantly or pulsed. Detection can be accomplished through the use of a single varied condition, or through a combination of conditions varied serially.

The response of a characteristic of the complex in the test medium to the varied condition or stimulus can be monitored to detect the complex. The characteristic can be, e.g., electrical conductance or Q (a resonant structure of a transmission line or changes in phase or amplitude of a signal propagated in the transmission line in the test medium).

In embodiments, the detection method comprises: (a) detecting a signal from a label, wherein the signal is correlated to a binding affinity between said probe and said target; (b) varying a condition of a test medium; (c) detecting a subsequent signal; and (d) comparing the signal and the subsequent signal. The varying and the detecting can be repeated at least once or performed only once.

Unlike certain prior art assays, the invention not only detects the presence of hybridization, but also provides qualitative and quantitative information regarding the nature of hybridization between a probe and target. Thus, the invention enables the practitioner to: (a) detect the presence of the target in the test medium; (b) detect allelic or heterozygous variance in the target; (c) quantitate the target; and (d) detect an extent of complementarity between the probe and the target.

The formation of the complex can be facilitated by intercalators, as disclosed in U.S. patent application Ser. No. 09/613,263, filed Jul. 10, 2000. The intercalators are optionally fluorescent.

Complex formation can also be facilitated by DNA or RNA binding proteins or peptides, or cations. In embodiments, a cationic moiety can be covalently bound to the probe.

It has been experimentally shown that hairpin formation in probes can be obviated at little or no cost to efficiency when practicing duplex or triplex hybridization with target at low temperatures, such as room temperature. Experiments have shown that it is possible to conjugate free bases onto the complementary bases of a probe prior to exposing that probe to target without inhibiting the rapid complexing of the probe with the target.

The inventors have previously disclosed specific homologous binding between antiparallel and parallel strands. The method of this invention increases the avidity and specificity of both Watson-Crick and homologous binding. Remarkably, conjugation actually increases the specificity of Watson-Crick binding by suppressing mismatch binding.

In a particularly remarkable embodiment of the invention, it was unexpectedly found that conjugating less than all of the guanosines of the probe with free cytosines contributed to increased specificity of the probe as compared to unconjugated similar probes. Additionally, it was unexpectedly found that slight conjugation, wherein less than 1 of the 4 Gs on the probe could have been conjugated with free Cs (assuming that every free C in the incubation mix had attached to a G in the probe, which is not likely), increased specificity for parallel probes, i.e., probes which are parallel to the orientation of the Watson-Crick complementary strand in the duplex target.

At higher concentrations of C in the incubation mix, antiparallel probes displayed increased Watson-Crick binding motif specificity.

As used herein, the phrase "increased specificity" means an increase in the difference in the signal between perfectly matched probe-target complexing and 1 bp mismatch probe-target complexing. Such specificity remarkably exists in respect of both Watson-Crick and homologous binding motifs.

Triplex assaying under conditions where free "Cs" are added to the test medium as not having been purified out after oligo conjugation does not appear to have an effect, though this has not yet been confirmed experimentally by assaying with conjugated oligos which have been purified before use.

The invention will be illustrated in more detail with reference to the following Example, but it should be understood that the present invention is not deemed to be limited thereto.

EXAMPLE 1

This example will show that nucleic acids conjugated with free bases or nucleosides bind other nucleic acids with greater avidity and greater specificity than do unconjugated nucleic acids under the same binding conditions.

Complementary sense and antisense 50-mer ssDNA target sequences, derived from exon 10 of the human cystic fibrosis gene (Nature 380, 207 (1996)) were synthesized on a DNA synthesizer (Expedite 8909, PerSeptive Biosystems) and purified by HPLC. SsDNA oligonucleotides were dissolved in ddH$_2$O and diluted to a concentration of 1 pmole/ml. Equimolar amounts of complementary oligonucleotides were heated at 95° C. for 10 min and allowed to anneal gradually in the presence of 10 mM Tris, pH 7.5, 1 mM EDTA and 100 mM NaCl, as the temperature cooled to 21° C. over 1.5 hours. DsDNA oligonucleotides were diluted in ddH$_2$O at a concentration of 1 pmole/ml.

SEQ ID NO:1 was a 50-mer dsDNA target sequence having a percent GC content of 52%.

The sequence for the sense strand of the wild-type target DNA (SEQ ID NO:1) was: 5'-GAG CAC CAT GAC AGA CAC TGT CAT CTC TGG TGT GTC CTA CGA TGA CTC TG-3'.

The sequence for the antisense strand of the wild-type target DNA (SEQ ID NO:1) was: 5'-CAG AGT CAT CGT AGG ACA CAC CAG AGA TGA CAG TGT CTG TCA TGG TGC TC-3'.

SEQ ID NO:2 was a 50-mer mutant dsDNA target sequence identical to SEQ ID NO:1, except for a one base pair mutation (underlined), at which the sense strand sequence CTC was changed to CTT.

The sequence for the sense strand of mutant SEQ ID NO:2 was: 5'-GAG CAC CAT GAC AGA CAC TGT CAT CTT TGG TGT GTC CTA CGA TGA CTC TG-3'.

The sequence for the antisense strand of mutant SEQ ID NO:2 was: 5'-CAG AGT CAT CGT AGG ACA CAC CAA AGA TGA CAG TGT CTG TCA TGG TGC TC-3'.

Probe No. 1 was a 15-mer ssDNA probe designed to be completely complementary to a 15 nucleotide segment of the sense strand of the 50-mer wild-type target DNA (SEQ ID NO:1). The directionality of the probe was opposite or antiparallel to that of the sense strand in the target.

The sequence for Probe No. 1 (SEQ ID NO:3) was: 5'-CAC CAG AGA TGA CAG-3'.

Samples of two pmoles of ssDNA Probe No. 1 in ddH$_2$O were heated at 95° C. for 10 minutes and allowed to cool to room temperature for 30 minutes in the presence of various concentrations of a free base, resulting in ssDNA probes containing conjugated bases. Duplicate samples of ssDNA Probe No. 1 were similarly denatured and cooled in the absence of added free bases to generate non-conjugated ssDNA probes. Two pmoles of these conjugated or non-conjugated ssDNA probes were then mixed with 2 pmoles of ssDNA target in the presence of 500 nM YOYO-1 and 0.5×TBE in a final reaction volume of 40 µl. The reaction mixtures were incubated at room temperature (21° C.) for 5 minutes, placed into a quartz cuvette, irradiated with an argon ion laser beam having a wavelength of 488 nm, and monitored for fluorescent emission. The intensity of fluorescence was plotted as a function of wavelength for each sample analyzed.

When the non-conjugated ssDNA Probe No. 1 was reacted with the 5 wild-type sense strand of SEQ ID NO:1 or with the 50-mer mutant sense strand of SEQ ID NO:2, in the presence of YOYO-1, antiparallel complementary ssDNA:ssDNA complexes formed (FIG. 1A). Remarkably, it appears that the conjugated probe bound its matched antiparallel complement with increased avidity while binding less to its mismatched complement. The fluorescent intensity emitted by the 1 bp T-G mismatched antiparallel complementary duplex (sense strand of SEQ ID NO:2+ Probe No. 1) was 45% lower than that obtained by the perfectly matched antiparallel complementary duplex (sense strand of SEQ ID NO:1+Probe No. 1). Control samples comprising each 50-mer ssDNA target plus 500 nM YOYO-1 exhibited levels of fluorescence which ranged from 92% to 93% lower than that observed with the perfectly matched duplexes (FIG. 1A). The level of fluorescence emitted by the 15-mer ssDNA Probe No. 1 plus 500 nM YOYO-1 was slightly greater than that produced by YOYO-1 alone.

When the ssDNA Probe No. 1 was reacted with the 50-mer wild-type antisense strand of SEQ ID NO:1 in the presence of YOYO-1, parallel homologous ssDNA:ssDNA complexes formed (FIG. 1B). The efficiency of matched parallel homologous ssDNA:ssDNA duplex formation was 14% lower than the efficiency of matched antiparallel complementary ssDNA:ssDNA duplex formation (compare FIGS. 1A and 1B). The 1 bp A-G mismatched parallel homologous duplex formed when the 50-mer mutant antisense strand of SEQ ID NO:2 was reacted with the ssDNA Probe No. 1 in the presence of YOYO-1, produced a fluorescent emission intensity that was 47% lower than that emitted by the perfectly matched parallel homologous duplex (FIG. 1B).

The 15-mer ssDNA Probe No. 1 contains six adenine bases. Conjugation of 2 pmoles of ssDNA Probe No. 1 with 3 pmoles of free thymine could result in 25% of the complementary A or 100% of the homologous T within Probe No. 1 bound to the added thymine. Complementary A-T binding is energetically preferred. Reaction of 2 pmoles of ssDNA Probe No. 1 (conjugated with 3 pmoles of thymine) with 2 pmoles of the wild-type antisense strand of ID NO:1 in the presence of YOYO-1 resulted in dramatically enhanced matched parallel homologous ssDNA:ssDNA complex formation (FIG. 1B). Twenty-five percent conjugation of the ssDNA probe with 3 pmoles of thymine increased parallel homologous complex formation between the perfectly homologous sequences by 78%. By contrast, the efficiency of formation of parallel homologous complexes containing a 1 bp A-G mismatch (antisense strand of SEQ ID NO:2+Probe No. 1) were increased by only 16% when Probe No. 1 was conjugated 25% with thymine than when non-conjugated Probe No. 1 was used (FIG. 1B). This corresponded to a 65% difference in fluorescent emission intensity for the 1 bp A-G mismatched parallel homologous complex compared to that observed for the perfectly matched parallel homologous complex when the T-conjugated Probe No. 1 was used. Conjugation of the ssDNA probe increased the specificity in discriminating between perfectly matched parallel homologous complexes and 1 bp mismatched parallel homologous complexes.

Remarkably, perfectly matched antiparallel complementary ssDNA:ssDNA complex formation was enhanced by 48% when Probe No. 1 conjugated 25% with thymine was reacted with the sense strand of SEQ ID NO:1 in the presence of YOYO-1 (FIG. 1A). The simultaneous interaction of an adenine in Probe No. 1 with the conjugated complementary thymine and the complementary T in the ssDNA target augmented formation of the perfectly matched antiparallel complementary complex. Remarkably, formation of the 1 bp T-G mismatched antiparallel complementary complex was very inefficient when T-conjugated Probe No. 1 was used, resulting in an 88% decrease in fluorescent emission intensity compared to that generated by the perfectly matched antiparallel complementary complex containing conjugated T (FIG. 1A). It is also remarkable that discrimination between perfectly matched and 1 bp mismatched antiparallel complementary ssDNA:ssDNA complexes was greatly enhanced by use of conjugated ssDNA probes in the presence of YOYO-1.

Twenty-five percent conjugation of Probe No. 1 with cytosine or guanosine also increased the efficiency of both antiparallel complementary and parallel homologous ssDNA:ssDNA complex formation in the presence of YOYO-1, as well as improved the specificity in differentiation between perfectly matched complexes and 1 bp mismatched complexes (data not shown).

Formation of ssDNA:ssDNA complexes comprising conjugated bases demonstrates nucleic acid recognition and interaction can be enhanced as to rate and specificity in respect of both complementary and homologous binding preferences by prior conjugation of a nucleic acid strand by free bases, nucleosides or their analogues.

While the invention has been described in detail and with reference to specific examples thereof, it will be apparent to one skilled in the art that various changes and modifications can be made therein without departing from the spirit and scope thereof.

What is claimed is:

1. In a method of forming a complex between a probe containing probe nucleobases and a target containing target nucleobases, comprising mixing said probe and said target under hybridizing conditions, the improvement wherein at least one blocking agent comprising at least one nucleobase is conjugated to said probe and not to said target prior to hybridizing said probe with said target, wherein said conjugation enhances an avidity and/or a specificity of said hybridizing by hindering said probe and/or said target from existing in a conformation antithetical to said hybridization.

2. The method of claim 1, wherein said conformation is a hairpin structure.

3. The method of claim 1, wherein said at least one blocking agent contains up to five nucleobases.

4. In a method of forming a complex between a probe containg probe nucleobases and a target containing target nucleobases, comprising mixing said probe and said target under hybridizing conditions, the improvement wherein at least one blocking agent comprising up to two nucleobases is conjugated to said probe and not to said target prior to hybridizing said probe with said target, wherein said conjugation enhances an avidity and/or a specificity of said hybridizing.

5. In a method of forming a complex between a probe containing probe nucleobases and a target containing target nucleobases, comprising mixing said probe and said target under hybridizing conditions, the improvement wherein at least one blocking agent comprising at least one nucleobase is conjugated to said probe and/or said target prior to hybridizing said probe with said target, wherein said at least one nucleobase is the only nucleobase contained in said at least one blocking agent, and said conjugation enhances an avidity and/or a specificity of said hybridizing.

6. The method of claim 5, wherein said at least one nucleobase is provided to said probe and/or said target as a free nucleobase, in a nucleoside or in a nucleotide.

7. The method of claim 5, wherein said at least one blocking agent is provided to said probe and/or said target as a free nucleobase.

8. The method of claim 5, wherein prior to said mixing, an amount of said at least one blocking agent is conjugated to said probe and/or to said target.

9. The method of claim 8, wherein said at least one nucleobase is provided in a quantity that is 1–200% of a number of said probe nucleobases that are Watson-Crick complements to said at least one nucleobase.

10. The method of claim 9, wherein said quantity is about 25% of said number of said probe nucleobases that are Watson-Crick complements to said at least one nucleobase.

11. The method of claim 8, wherein said at least one nucleobase is provided in a quantity that is 1–200% of a number of said probe nucleobases that are identical to said at least one nucleobase.

12. The method of claim 11, wherein said quantity is about 100% of said number of said probe nucleobases that are identical to said at least one nucleobase.

13. The method of claims 8, wherein said at least one nucleobase is provided in a quantity that is 1–200% of a number of said target nucleobases that are Watson-Crick complements to said at least one nucleobase.

14. The method of claim 13, wherein said quantity is about 25% of said number of said target nucleobases that are Watson-Crick complements to said at least one nucleobase.

15. The method of claim 8, wherein said at least one nucleobase is provided in a quantity that is 1–200% of a number of said target nucleobases that are identical to said at least one nucleobase.

16. The method of claim 15, wherein said quantity is about 100% of said number of said target nucleobases that are identical to said at least one nucleobase.

17. The method of claim 1, wherein said probe nucleobases are arranged in a probe sequence of interspersed purines and pyrimidines, and said target nucleobases are arranged in a target sequence at least partially complementaly to said probe sequence.

18. The method of claim 1, wherein said probe has a sugar phosphate backbone.

19. The method of claim 1, wherein a backbone of said probe is uncharged or positively charged.

20. The method of claim 1, wherein said target is single-stranded DNA or single-stranded RNA.

21. The method of claim 1, wherein said target is double-stranded DNA, double-stranded RNA or DNA:RNA.

22. The method of claim 1, wherein said at least one blocking agent consists of a nucleobase, a nucleoside or a nucleotide.

23. The method of claim 1, said at least one blocking agent consists of a nucleobase.

24. The method of claim 1, wherein said at least one blocking agent is a naturally-occurring nucleobase selected from the group consisting of A, T, C, G and U.

25. The method of claim 1, wherein said at least one blocking agent is a synthetic nucleobase analogue.

26. The method of claim 1, wherein said probe has a probe directionality parallel to a target strand directionality of said target.

27. The method of claim 1, wherein said probe has a probe directionality anti-parallel to a target strand directionality of said target.

28. The method of claim 1, further comprising detecting said complex.

29. The method of claim 28, wherein said complex is formed with at least one of said probe and said target bound to a substrate, surface or biochip.

30. The method of claim 28, wherein said complex is detected by a change in a signal associated with a label.

31. The method of claim 30, wherein said label is at least one member selected from the group consisting of a spin label, a fluorophore, a chromophore, a chemiluminescent agent, an electro-chemiluminescent agent, a radioisotope, an enzyme, a hapten, an antibody and a labeled antibody.

32. The method of claim 28, wherein said complex is detected by analyzing an electronic characteristic of said complex.

33. The method of claim 28, wherein said detecting is conducted in a test medium and under a varied condition, wherein said varied condition is a member selected from the group consisting of: (a) a change in nonaqueous components of said test medium, (b) a change in a pH of said test medium, (c) a change in a salt concentration of said test medium, (d) a change of an organic solvent content of said test medium (e) a change in a formamide content of said test medium, (f) a change in a temperature of said test medium, (g) a change in chaotropic salt concentration in said test medium, (h) a change in an electric current (i) a change in a number of photons in the test medium, and (j) a change in an electrical property of the test medium.

34. The method of claim 33, wherein a laser beam is applied to said test medium to effect said change in the number of photons.

35. The method of claim 33, wherein said electrical property is electrical conductance.

36. The method of claim 33, wherein said electrical property is Q, a resonant structure of a transmission line or changes in phase or amplitude of a signal propagated in said transmission line in said test medium.

37. The method of claim 33, wherein said complex is detected under serially varied conditions.

38. The method of claim 30, wherein said label is added free in solution to said test medium.

39. The method of claim 28, further comprising:

(a) detecting a signal from a label, wherein said signal is correlated to a binding affinity between said probe and said target;

(b) varying a condition of a test medium;

(c) detecting a subsequent signal; and (d) comparing said signal and said subsequent signal.

40. The method of claim 28, wherein said target is quantitated.

41. The method of claim 28, wherein an extent of complementarity between said probe and said target is detected.

42. The method of claim 1, wherein formation of said complex is facilitated by at least one intercalator.

43. The method of claim 1, wherein: (a) said complex is formed in a presence of at least one other probe containing a sequence of nucleobases complementary to a secondary target sequence different from a primary target sequence of said target; (b) said other probe differs from said probe by only a single nucleobase; (c) said other probe forms a complex with said target; and (d) said target is detected.

44. The method of claim 1, wherein the probe and the target hybridize in accordance with a Watson-Crick motif to form duplex, triplex or quadruplex nucleic acid complexes.

45. The method of claim 1, wherein the probe and the target hybridize in accordance with a homologous binding motif to form duplex, triplex or quadruplex nucleic acid complexes.

46. The method of claim 1, wherein said hybridizing is conducted in a homogeneous medium.

* * * * *